US012169884B2

United States Patent
Tanaka et al.

(10) Patent No.: US 12,169,884 B2
(45) Date of Patent: *Dec. 17, 2024

(54) IMAGE PROCESSING APPARATUS FOR GENERATING A HIGHLY VISIBLE THREE-DIMENSIONAL IMAGE FROM TWO MEDICAL IMAGES

(71) Applicant: CANON KABUSHIKI KAISHA, Tokyo (JP)

(72) Inventors: Toru Tanaka, Chiba (JP); Kazuhiro Miyasa, Chiba (JP); Kiyohide Satoh, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 437 days.

This patent is subject to a terminal disclaimer.

(21) Appl. No.: 17/497,721

(22) Filed: Oct. 8, 2021

(65) Prior Publication Data

US 2022/0028134 A1 Jan. 27, 2022

Related U.S. Application Data

(63) Continuation of application No. PCT/JP2020/011469, filed on Mar. 16, 2020.

(30) Foreign Application Priority Data

Apr. 10, 2019 (JP) ................................ 2019-075075

(51) Int. Cl.
*G06T 7/30* (2017.01)
*G06T 3/40* (2006.01)
(Continued)

(52) U.S. Cl.
CPC .............. *G06T 11/008* (2013.01); *G06T 3/40* (2013.01); *G06T 7/0012* (2013.01); *G06T 7/30* (2017.01);
(Continued)

(58) Field of Classification Search
CPC .......... A61B 6/00; A61B 6/03; G06T 11/008; G06T 3/40; G06T 7/0012; G06T 7/30;
(Continued)

(56) References Cited

U.S. PATENT DOCUMENTS

| 11,437,136 B2* | 9/2022 | Miyasa .................. G16H 30/40 |
| 2008/0205717 A1* | 8/2008 | Reeves ................. G06T 11/008 |
| | | 382/128 |

(Continued)

FOREIGN PATENT DOCUMENTS

| JP | 2005136594 A | 5/2005 |
| JP | 2019046057 A | 3/2019 |
| WO | 2018043575 A1 | 3/2018 |

OTHER PUBLICATIONS

R. Sakamoto, et. al. "Temporal subtraction system for detecting bone metastasis using LDDMM;" preliminary study, CARS2014.

*Primary Examiner* — Amandeep Saini
*Assistant Examiner* — Caroline Tabancay Duffy
(74) *Attorney, Agent, or Firm* — Canon U.S.A., Inc. IP Division

(57) ABSTRACT

An image processing apparatus that generates a three-dimensional image as a subtraction image from a first medical image and a second medical image which are three-dimensional images obtained by imaging a subject, the image processing apparatus includes an acquisition unit configured to acquire the first medical image and the second medical image, a determination unit configured to determine a resolution of the subtraction image, and, a subtraction image generation unit configured to generate the subtraction image having the resolution determined by the determination unit, wherein the determination unit determines a resolution of at least one axial direction among three axial directions configuring the resolution of the subtraction (Continued)

image, based on a resolution of the first medical image and a predetermined first resolution.

19 Claims, 5 Drawing Sheets

(51) Int. Cl.
*G06T 7/00* (2017.01)
*G06T 11/00* (2006.01)
(52) U.S. Cl.
CPC .............. *G06T 2207/10081* (2013.01); *G06T 2207/20224* (2013.01); *G06T 2207/30004* (2013.01); *G06T 2207/30168* (2013.01)
(58) Field of Classification Search
CPC . G06T 2207/10081; G06T 2207/20224; G06T 2207/30004; G06T 2207/30168; G06T 7/0016; G06T 2207/10072; G06T 2207/10136; G06T 1/00
See application file for complete search history.

(56) References Cited

U.S. PATENT DOCUMENTS

| | | | | |
|---|---|---|---|---|
| 2011/0268328 | A1* | 11/2011 | Bar-Aviv ................. | G06T 5/70 382/128 |
| 2011/0274330 | A1* | 11/2011 | Mori ................... | A61B 6/5235 382/131 |
| 2011/0305405 | A1* | 12/2011 | Kawamura .............. | G06T 3/14 382/294 |

* cited by examiner

FIG.3
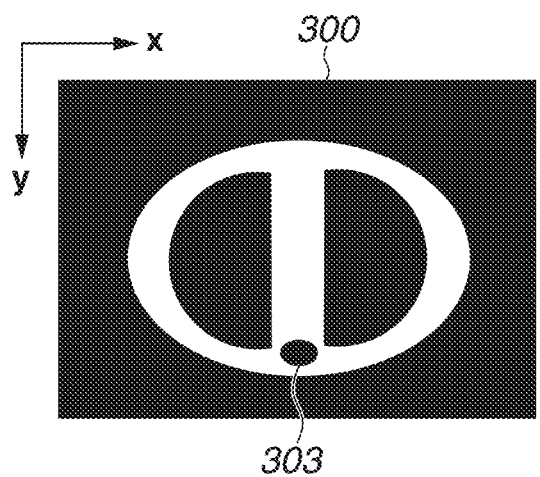
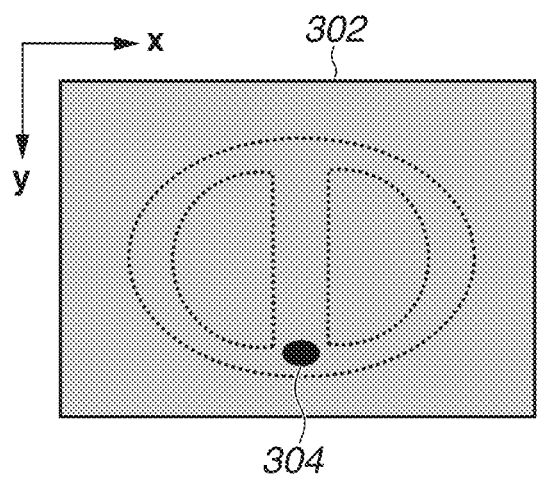
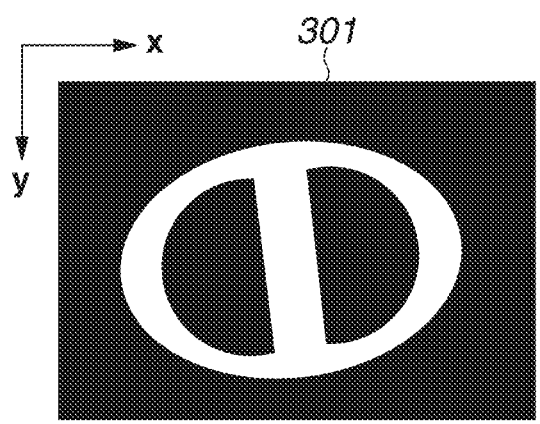

IMAGE PROCESSING APPARATUS FOR GENERATING A HIGHLY VISIBLE THREE-DIMENSIONAL IMAGE FROM TWO MEDICAL IMAGES

CROSS-REFERENCE TO RELATED APPLICATIONS

This application is a Continuation of International Patent Application No. PCT/JP2020/011469, filed Mar. 16, 2020, which claims the benefit of Japanese Patent Application No. 2019-075075, filed Apr. 10, 2019, both of which are hereby incorporated by reference herein in their entirety.

BACKGROUND OF THE INVENTION

Field of the Invention

The disclosure of the present specification relates to an image processing apparatus, an image processing method, and a storage medium.

Background Art

In the medical field, there have been attempts to present users subtraction images generated from two images captured at different times from each other by various modalities to visualize time courses of lesions and the like.

A non-patent literature (NPL) 1 discusses a technique for displaying a subtraction image generated from two three-dimensional images captured by a computed tomography (CT) apparatus as a two-dimensional tomographic image. The NPL 1 also discusses a technique for generating and displaying a two-dimensional projection image obtained by projecting using a luminance value of a subtraction image in a direction parallel to a slice plane (generally, a direction orthogonal to a body axis of a subject in the CT).

CITATION LIST

Non Patent Literature

NPL 1: R. Sakamoto, et. al, Temporal subtraction system for detecting bone metastasis using LDDMM: preliminary study, CARS2014.

However, according to the techniques discussed in the NPL 1, in a case where a difference image is generated from two three-dimensional images obtained with large slice intervals, a slice interval of the difference image also becomes large. Accordingly, there is an issue that, in a case where a projection image obtained by projecting using a luminance value of a difference image in a direction parallel to a slice plane is displayed on a display unit, the displayed image is difficult to see.

SUMMARY OF THE INVENTION

In view of the above-described issue, the disclosure of the present specification is directed to generation of a subtraction image having high visibility even in a case where the subtraction image is projected in a direction parallel to a slice plane.

Not limited to the above, the disclosure of the present specification is also directed to the provision of functions and effects that are derived by each configuration according to below-described exemplary embodiments of the present invention and cannot be obtained from conventional techniques.

According to an aspect of the present invention, an image processing apparatus that generates a three-dimensional image as a subtraction image from a first medical image and a second medical image which are three-dimensional images obtained by imaging a subject, the image processing apparatus includes an acquisition unit configured to acquire the first medical image and the second medical image, a determination unit configured to determine a resolution of the subtraction image, and, a subtraction image generation unit configured to generate the subtraction image having the resolution determined by the determination unit, wherein the determination unit determines a resolution of at least one axial direction among three axial directions configuring the resolution of the subtraction image, based on a resolution of the first medical image and a predetermined first resolution.

Further features of the present invention will become apparent from the following description of exemplary embodiments with reference to the attached drawings.

BRIEF DESCRIPTION OF THE DRAWINGS

FIG. 3 is a diagram illustrating examples of axial cross sections of original images and a subtraction image.

DESCRIPTION OF THE EMBODIMENTS

Various exemplary embodiments of an image processing apparatus in the present specification will be described in detail below with reference to the attached drawings. Components described in the exemplary embodiments are merely examples, and the technical scope of the image processing apparatus described in the present specification is determined by the scope of claims and is not limited by the individual exemplary embodiments described below. The disclosure of the present specification is not limited to the below described exemplary embodiments and can be modified in various ways without departing from the gist of the disclosure of the present specification. An example modification of the present invention includes an organic combination of the exemplary embodiments. In this respect, the disclosure of the present specification does not intend to exclude those modifications that are not discussed in the present specification. In other words, the exemplary embodiments described below, modifications, and combinations thereof are all included in the exemplary embodiments described in the present specification.

First Exemplary Embodiment

An image processing apparatus according to a first exemplary embodiment aligns two images captured at different times from each other and generates a subtraction image. In a case where slice intervals of the two images (original images) are large, the image processing apparatus according to the present exemplary embodiment adjusts a resolution in a direction orthogonal to a slice plane of a subtraction image (namely, a slice interval of the subtraction image) to a predetermined high resolution, to generate a subtraction image.

A configuration and processing according to the present exemplary embodiment are described below with reference to FIGS. 1 to 4.

Figure 1:
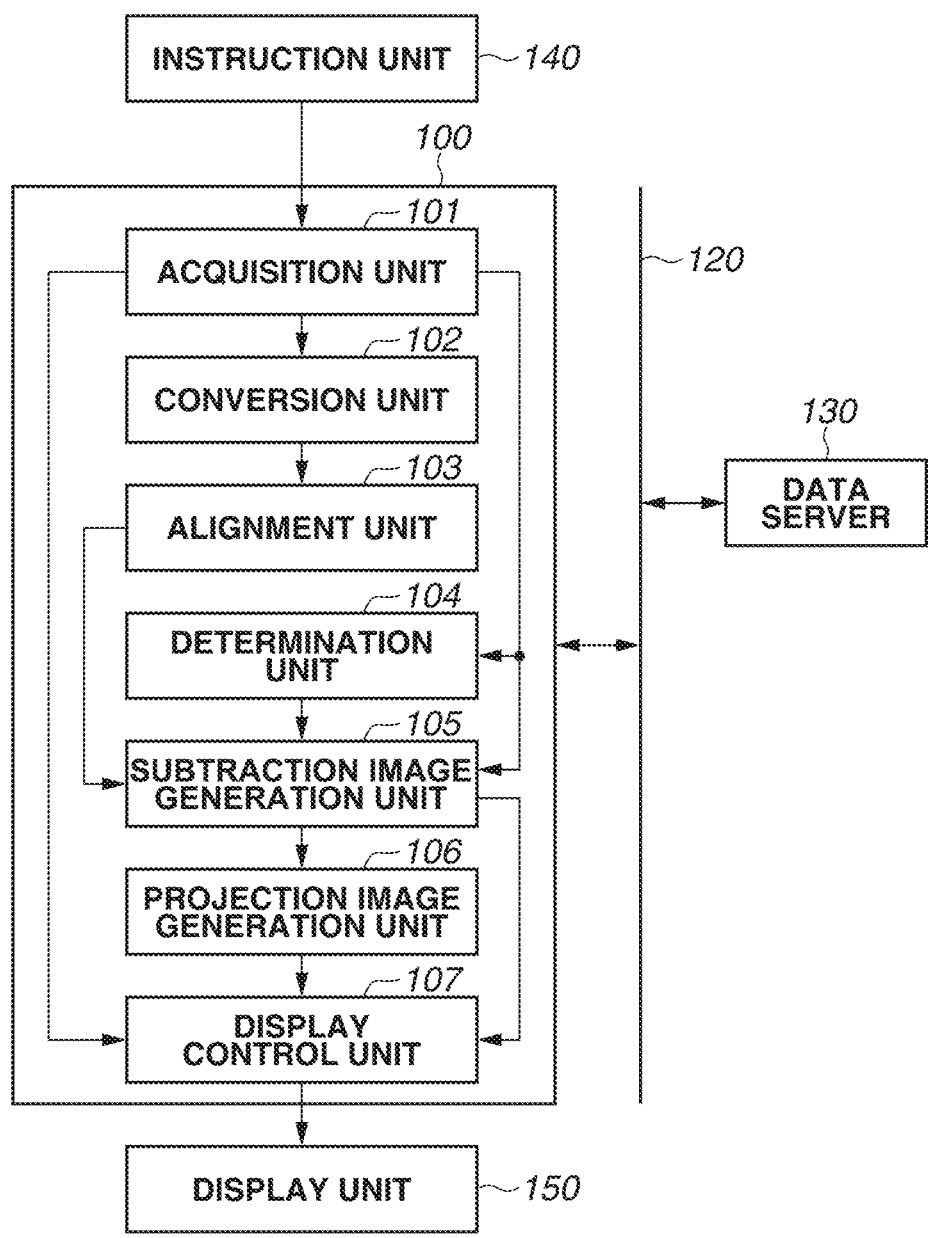
FIG. 1 is a diagram illustrating a device configuration of an image processing system according to a first exemplary embodiment.

FIG. 1 illustrates a configuration of an image processing system according to the present exemplary embodiment. As illustrated in FIG. 1, an image processing apparatus 100 according to the present exemplary embodiment is connected to a data server 130 via a network 120.

The data server 130 stores a plurality of medical images. In the following descriptions, the data server 130 stores a plurality of three-dimensional tomographic images which are obtained by imaging a subject in advance under different conditions (different modalities, imaging modes, dates and times, positions, and the like), as a first medical image and a second medical image. According to the present exemplary embodiment, the first medical image and the second medical image are described as three-dimensional tomographic images (three-dimensional medical images) captured and obtained by an X-ray computed tomography (CT) apparatus.

Figure 5:
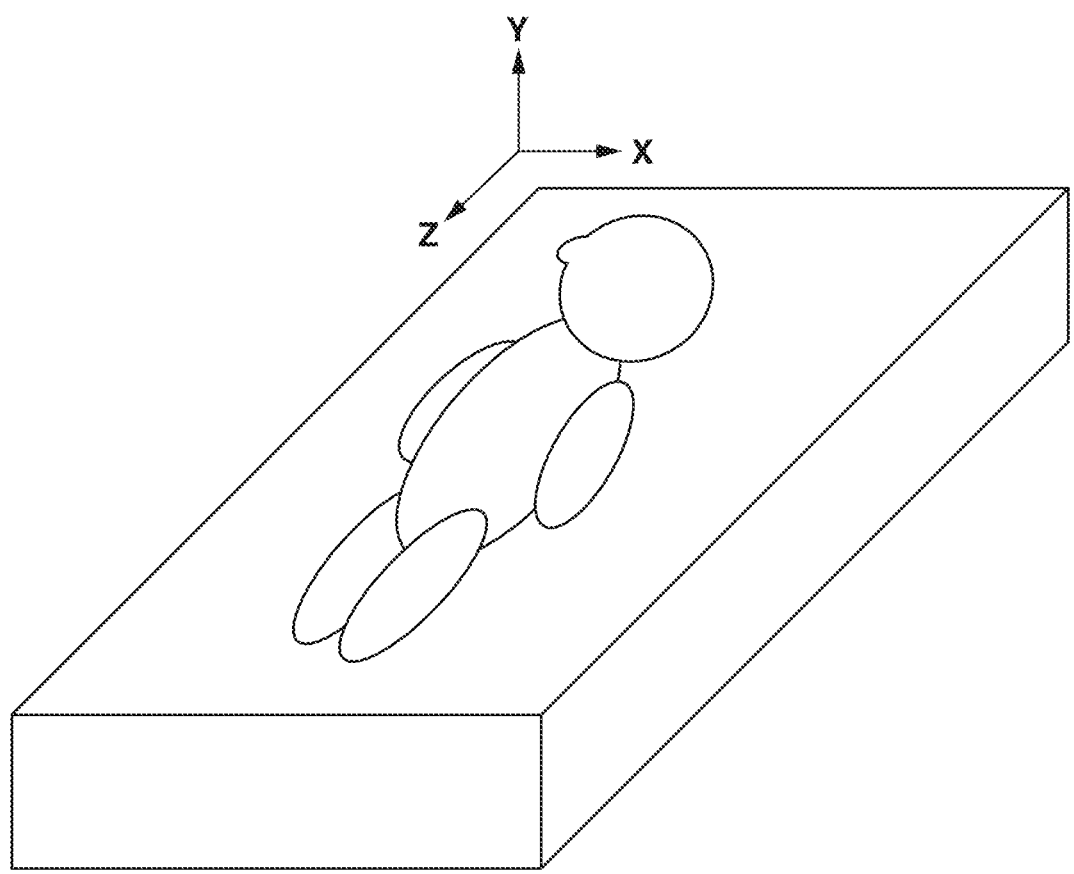
FIG. 5 is a diagram illustrating an example of a setting of coordinate axes according to the present exemplary embodiment.

According to the present specification, an axis representing a direction from a right hand to a left hand of a subject, an axis representing a direction from a back to a front of the subject, and an axis representing a direction from a head to feet of the subject are defined as an X-axis, a Y-axis, and a Z-axis, respectively, as illustrated in FIG. 5. An XY cross section, a YZ cross section, and a ZX cross section are defined as an axial plane, a sagittal plane, and a coronal plane, respectively. In other words, an X-axis direction is a direction orthogonal to the sagittal plane (hereinbelow, a sagittal direction). A Y-axis direction is a direction orthogonal to the coronal plane (hereinbelow, a coronal direction). Further, a Z-axis direction is a direction orthogonal to the axial plane (hereinbelow, an axial direction). In a case of a CT image formed by a group of two-dimensional slice images, a slice plane of the image represents the axial plane, and a direction orthogonal to the slice plane (hereinbelow, a slice direction) represents the axial direction. The above-described method of setting a coordinate system is an example, and another definition may be used.

A modality which captures a three-dimensional tomographic image may be a magnetic resonance imaging (MRI) apparatus, a three-dimensional ultrasonic imaging apparatus, a photoacoustic tomography apparatus, a positron emission tomography (PET)/single photon emission computed tomography (SPECT) apparatus, an optical coherence tomography (OCT) apparatus, and the like. Further, the first medical image and the second medical image may be any image as long as it is a three-dimensional tomographic image to be used for generating a subtraction image. For example, the first medical image and the second medical image may be captured by different modalities or different imaging modes around the same time. The first medical image and the second medical image may be images of the same patient captured by the same modality in the same position at different times and dates for a follow-up. The first medical image and the second medical image are three-dimensional medical images (three-dimensional tomographic images) each formed by a group of two-dimensional tomographic images, and a position and an orientation of each two-dimensional tomographic image are stored in the data server 130 after being converted into a reference coordinate system (a coordinate system in a space based on the subject). The first medical image and the second medical image expressed in the reference coordinate system are input to the image processing apparatus 100 according to an instruction of a user who operates an instruction unit 140.

The image processing apparatus 100 performs image processing in response to a processing request from a user via the instruction unit 140 and outputs a processing result to a display unit 150, and functions as an terminal device operated by a user, such as a doctor, in image interpretation. Specifically, the image processing apparatus 100 acquires the first medical image and the second medical image as a pair of images to be an image processing target from the data server 130 based on a request from the user via the instruction unit 140. Then, the image processing apparatus 100 performs registration processing on the two images, and generates and outputs a subtraction image to the display unit 150. The image processing apparatus 100 is configured with components described below. An acquisition unit 101 acquires information about the first medical image and the second medical image input to the image processing apparatus 100. A conversion unit 102 converts resolutions of the first medical image and the second medical image into a predetermined resolution (hereinbelow, a processing resolution). An registration unit 103 performs registration processing between the first medical image and the second medical image, which have been subjected to resolution conversion (hereinbelow, a first conversion image and a second conversion image), and calculates a displacement field between the images. A determination unit 104 determines a resolution of a subtraction image to be output (hereinbelow, an output resolution). A subtraction image generation unit 105 generates a subtraction image between a second deformed image, which is obtained by deforming the second medical image based on the acquired displacement field to coincide the second medical image with the first medical image, and the first medical image based on the output resolution. A projection image generation unit 106 generates a projection image (hereinbelow, a subtraction projection image) which is obtained by two-dimensionally projecting a luminance value of the subtraction image. A display control unit 107 controls outputting of the generated subtraction image and the generated subtraction projection image and the like to the display unit 150.

The display unit 150 is configured with an arbitrary device, such as a liquid crystal display (LCD) and a cathode ray tube (CRT) display, and displays a medical image and the like for a doctor to interpret images. Specifically, the display unit 150 displays cross sectional images of the first medical image and the second medical image acquired from the image processing apparatus 100. The display unit 150 also displays a cross sectional image of a subtraction image and a subtraction projection image which are generated in the image processing apparatus 100.

Figure 2:
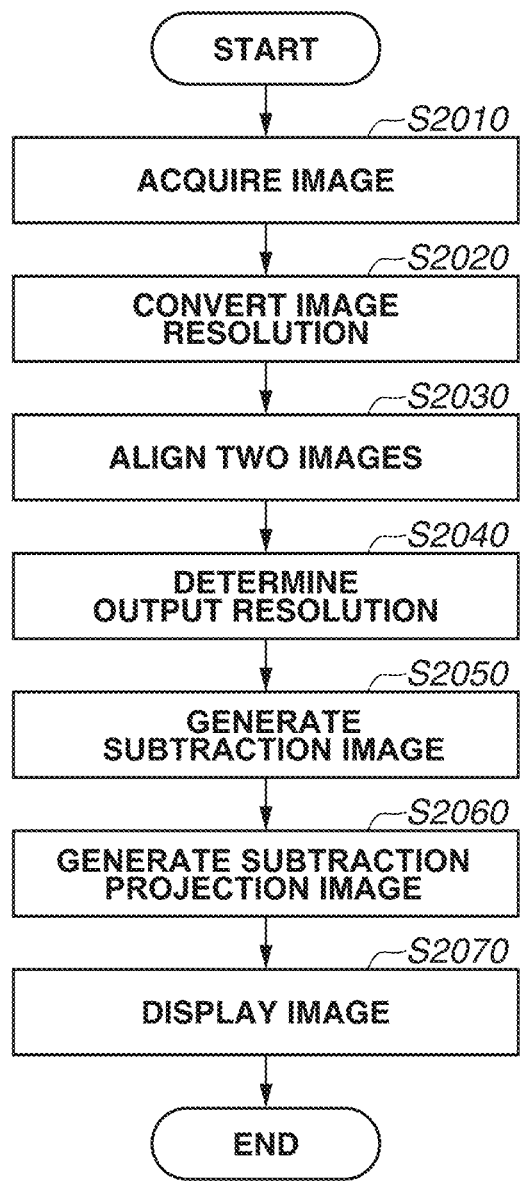
FIG. 2 is a flowchart illustrating an entire processing procedure according to the first exemplary embodiment.

FIG. 2 is a flowchart illustrating an entire processing procedure that is performed by the image processing apparatus 100.

(S2010) (Acquire Image)

In step S2010, the acquisition unit 101 acquires a first medical image and a second medical image, which are specified by a user, from the data server 130 via the instruction unit 140. Then, the acquisition unit 101 outputs the first medical image and the second medical image to the conversion unit 102, the subtraction image generation unit 105, and the display control unit 107.

(S2020) (Convert Image Resolution)

In step S2020, the conversion unit 102 converts resolutions of the first medical image and the second medical image into a processing resolution and acquires a first conversion image and a second conversion image.

For example, in a case where voxel sizes of the first medical image and the second medical image which are original images of a subtraction image are anisotropic, the conversion unit 102 acquires the first conversion image and the second conversion image having voxel sizes converted to be isotropic, whereby registration between images in subsequent processing can be performed with high accuracy. More specifically, for example, in a case where the first medical image and the second medical image are CT images, since a resolution in the slice plane (for example, the sagittal direction or the coronal direction) is higher than a resolution in the slice direction (the axial direction), the conversion unit 102 performs upsampling on voxels in the slice direction in accordance with the resolution in the slice plane. A known image processing method can be used for interpolation of a density value in the resolution conversion.

According to the present exemplary embodiment, the processing resolution is set to 1 mm in each of the three-dimensional axial directions in order for calculation of a subtraction in details between the images, and the first conversion image and the second conversion image having voxel sizes converted to be isotropic by the resolution conversion are acquired. The processing resolution may be a value other than 1 mm, and the first conversion image and the second conversion image may not be converted to be isotropic, as long as a subtraction in details between the images can be adequately calculated with the resolution, and it is sufficient that the resolution is converted to an extent that registration between images in the subsequent processing can be performed with high accuracy. Further, in a case where resolution conversion processing is not necessary, such as a case in which the resolutions of the first medical image and the second medical image are the processing resolution at a stage when they are acquired in step S2010, the resolution conversion does not necessarily have to be performed. Then, the conversion unit 102 outputs the first conversion image and the second conversion image to the registration unit 103.

(S2030) (Align Two Images)

In step S2030, the registration unit 103 aligns the first conversion image and the second conversion image by substantially coinciding voxels representing the same region with each other and acquires a displacement field which associates positions between the images. Then, the registration unit 103 outputs information about the displacement field obtained by the registration to the subtraction image generation unit 105.

According to the present exemplary embodiment, registration between images refers to processing for calculating a displacement field for displacing each voxel position of one image to correspond to voxel positions of the other image.

For example, in a case where there are two images captured at different times from each other, a displacement field is calculated by displacing each voxel position of one image which is captured prior to the other image to correspond to voxel positions of the other image. More specifically, if the second medical image is an image captured prior to the first medical image according to the present exemplary embodiment, each voxel position of the second conversion image is displaced to be aligned to the first conversion image, and thus a displacement vector field in each voxel position is acquired. In other words, the displacement field generated as described above is an image (the second deformed image) storing displacement vectors of every voxel positions in the first conversion image based on the first conversion image and has the same resolution and the same voxel number as those of the first conversion image. Therefore, in a case where the processing resolution is 1 mm isotropic, a displacement field is also an isotropic displacement vector field of 1 mm. Accordingly, the displacement field maintains an information amount from which the subtraction in details between the images can be calculated.

According to the present exemplary embodiment, registration of two images is performed using a known image processing method. For example, registration is performed by deforming one of the images in such a manner that image similarity between the images is increased. As the image similarity, a known method, such as a sum of squared subtraction (SSD), a mutual information amount, and a mutual correlation coefficient, which are generally used, can be used. As a model of image deformation, a known deformation model, such as a deformation model based on a radial basis function such as thin plate spline (TPS), free form deformation (FFD), and large deformation diffeomorphic metric mapping (LDDMM), can be used.

(S2040) (Determine Output Resolution)

In step S2040, the determination unit 104 determines an output resolution based on the resolution of the first medical image and the processing resolution used in step S2020.

Then, the determination unit 104 outputs a value of the determined output resolution to the subtraction image generation unit 105.

Processing in which the determination unit 104 determines the output resolution is described in details.

Examples of a method commonly used for generating a subtraction image between two images include a method for generating a subtraction image in a form in which positions of an image (the first medical image according to the present exemplary embodiment) serving as a reference for registration in the two images and the subtraction image are associated to each other at each voxel. In this method, the subtraction image is generated with the same resolution and the same number of voxels as the image (the first medical image) serving as the reference for registration. Accordingly, for example, in a case where a user wants to check positions of a two-dimensional tomographic image included in the first medical image and a two-dimensional tomographic image included in the subtraction image in association with each other, the positions can be easily displayed in an associated manner.

However, in a case where the subtraction projection image which is obtained by two-dimensionally projecting the subtraction image in a direction parallel to the slice plane and a cross sectional image which is obtained by cutting the subtraction image at an arbitrary cross section including the sagittal plane or the coronal plane different from the slice plane (the axial plane) are generated and displayed, the following issue arises.

Specifically, if a slice interval of the first image is large, a slice interval of the subtraction image also becomes large. Accordingly, there is an issue that, while the resolution is sufficient in a case where a cross sectional image in the slice plane of the subtraction image is displayed on the display unit, the resolution becomes low in the slice direction in a case where the subtraction projection image is displayed on the display unit. This issue arises because in a case where three-dimensional tomographic images are acquired by various modalities, resolutions of the images often do not match with each other in all axial directions. For example, in a case of an X-ray CT apparatus, a resolution (a slice interval) in the slice direction (the axial direction) is often lower than a resolution in a slice in-plane direction (for example, the sagittal direction or the coronal direction) in order to reduce an exposure dose and a data amount.

According to the present exemplary embodiment, the resolution in the slice plane of the output resolution is matched with the resolution of the first image, and thus the first image and the subtraction image can be displayed in association with each other. Meanwhile, the resolution in the slice direction of the output resolution is determined in such a manner that the subtraction projection image does not become a rough image. For example, in a case where the slice plane of a three-dimensional image is defined by the X-axis and the Y-axis (for example, the sagittal direction and the coronal direction), and the slice direction (the axial direction) is defined by the Z-axis, resolutions of the X-axis and the Y-axis (in the slice plane) among the three axes forming the output resolution are determined to be matched with the resolutions of the X-axis and the Y-axis of the resolution of the first medical image. Meanwhile, the resolution of the Z-axis (the slice direction) is determined based on the resolution of the Z-axis of the first medical image and a predetermined resolution (hereinbelow, a first resolution) at which the subtraction in details between the images can be calculated.

More specifically, a higher (finer) one of the two resolutions, i.e., the resolution of the Z-axis of the first medical image and the first resolution, is set as the output resolution of the Z-axis (namely, the resolution of the Z-axis of the subtraction image). In other words, in a case where the resolution of the Z-axis of the first medical image is "lower than the first resolution", the output resolution of the Z-axis is set to the same resolution as the first resolution. On the other hand, in a case where the resolution of the Z-axis of the first medical image is "the same as or higher than the first resolution", the output resolution of the Z-axis is set to the same resolution as the resolution of the Z-axis of the first medical image. In other words, the output resolution is determined to be a resolution which is obtained by correcting the resolution in the slice direction of the first medical image serving as the reference of the subtraction image, based on the first resolution which is a high resolution, to prevent the resolution from being low as much as possible.

According to the present exemplary embodiment, a value of the processing resolution is used as the first resolution. In other words, an upper limit value of the output resolution in the slice direction is set as the processing resolution. Specifically, if the processing resolution is 1 mm isotropic, 1 mm is used as the first resolution. Since the upper limit value of the resolution (the first resolution) in the slice direction of the output resolution is matched with the processing resolution, the output resolution in the slice direction is also matched with the resolution of the displacement field obtained by registration processing as described in step S2030. As described in step S2030, the displacement field is generated at the resolution (1 mm) at which the subtraction in details between the images can be calculated. Thus, the upper limit value of the output resolution in the slice direction is set to a value not increasing a size of each voxel of the subtraction projection image, and also is set as a value which can express the subtraction in details between the images as an information amount. Since the upper limit value (a maximum value) is set to a value of the resolution in the slice direction of the output resolution, the resolution in the slice direction of the subtraction projection image can be set high even in a case where the slice interval of the first medical image is large (the resolution in the slice direction is low). In a case where the slice interval of the first medical image is originally small (the resolution in the slice direction is high), the resolution in the slice direction of the subtraction projection image can be set high as it is. Accordingly, the present exemplary embodiment can determine a more appropriate resolution and thus generate a subtraction projection image with high visibility as compared with a method for always generating a subtraction image at a predetermined resolution regardless of the resolution of the first medical image.

The value to be used as the first resolution is an example and not limited to the above-described one. In other words, the first resolution does not have to be matched with the value of the processing resolution and does not have to be 1 mm. It is desirable that the first resolution has a predetermined value of 0.5 mm or more and 2.0 mm or less. According to the above, the resolution can be appropriately set even in a case where, for example, a time course of a bone portion of a subject is observed.

In a case where the resolution in the slice direction of the first medical image is 5 mm, the resolution of the first medical image is lower than the processing resolution in the slice direction. Thus, a value in the slice direction of the output resolution is set to 1 mm. On the other hand, in a case where the resolution in the slice direction of the first medical image is 0.5 mm, the resolution of the first medical image is higher than the processing resolution in the slice direction. Thus, the value in the slice direction of the output resolution is set to 0.5 mm.

A determination method of the output resolution is not limited to the above-described one. For example, the value in the slice direction of the output resolution may be determined based on three resolutions including the resolution in the slice direction of the second medical image. In other words, the value in the slice direction of the output resolution may be determined to be a resolution that is obtained by correcting, based on the first resolution and the resolution in the slice direction of the second medical image, the resolution in the slice direction of the first medical image serving as the reference of the subtraction image. More specifically, the value in the slice direction of the output resolution may be a minimum value (a highest resolution) among the three resolutions. Accordingly, the value in the slice direction of the output resolution can be matched with a resolution including a largest amount of information, namely the highest resolution, among the resolution in the slice direction of the first medical image, the resolution in the slice direction of the second medical image, and the processing resolution.

Not limited to the value in the slice direction (the axial direction) of the output resolution, values in the slice plane (a value of the X-axis (the sagittal direction) and a value of the Y-axis (the coronal direction) in this example) may be calculated based on the resolution of the first medical image and the processing resolution. In other words, the resolution in at least one axial direction among the three axial directions forming the resolution of the subtraction image is determined based on the resolution of the first medical image and the predetermined first resolution.

Accordingly, it is possible to generate the subtraction image and the subtraction projection image having resolutions appropriately high in all the axial directions and having high visibility.

The output resolution in the slice direction may be not the minimum value of the first medical image and the processing resolution (or a combination of a plurality of resolutions including the first medical image and the processing resolution) but an intermediate value, such as an average value thereof and an average value weighted for each resolution.

For example, an average value of the first medical image, the second medical image, and the processing resolution is calculated, and thus the output resolution in the slice direction can be set to a value closer to that of the first medical image and the second medical image than in a case of the minimum value even in a case where the resolutions of the first medical image and the second medical image are extremely low. In other words, it is possible to reduce a possibility of generating a subtraction image and a subtraction projection image having an unnecessarily high resolution.

More specifically, in a case where the slice intervals of the first medical image and the second medical image are both extremely large (for example, 10 mm), resolutions themselves of original images from which a subtraction is calculated are extremely low. Consequently, registration itself becomes also inaccurate. Thus, even in a case where the resolution of the displacement field obtained by the registration is as fine as 1 mm, the information amount included therein is almost the same as that in a rough displacement field. Consequently, a subtraction projection image obtained as a result is based on a rough subtraction. In other words, if the output resolution in the slice direction is matched with the processing resolution (1 mm) which is the minimum value in a plurality of the resolutions, the subtraction image and the subtraction projection image having the unnecessarily high resolutions are generated.

However, even in the above-described case, a possibility of generating the subtraction image and the subtraction projection image having the unnecessarily high resolutions can be reduced by determining the average value and the like as the output resolution.

Even in a case where the slice intervals of the first medical image and the second medical image are both extremely small, the output resolution in the slice direction can be set to a value closer to that of the first medical image or the second medical image than a case of using the minimum value.

More specifically, in a case where the slice intervals of the first medical image and the second medical image are both extremely small (for example, 0.1 mm), the displacement field based on registration can be obtained only at a resolution of 1 mm. Thus, the subtraction projection image can be obtained only with the information amount of the resolution of the displacement field (however, it is sufficient to calculate the subtraction in details between the images as described above). In other words, if the output resolution in the slice direction is matched with the resolution (0.1 mm) of the first medical image, which is the minimum value in the combinations of the plurality of resolutions, the subtraction image and the subtraction projection image having the unnecessarily high resolutions are generated.

However, even in the above-described case, a possibility of generating the subtraction image and the subtraction projection image having the unnecessarily high resolutions can be reduced by calculating the average value of the combinations of the plurality of resolutions.

In the determination method of the output resolution, in a case where a predetermined condition is satisfied, the above-described normal processing for setting the minimum value is performed, and only in a case where the predetermined condition is not satisfied, the average value can be set. More specifically, the predetermined condition is regarded as a first condition, and the first condition is set in such a manner that the resolution in the slice direction of the first medical image is equal to or more than a first threshold value (for example, equal to or more than 0.4 mm) and less than a second threshold value (for example, less than 7 mm). For example, in a case where the resolution of the first medical image satisfies the first condition, the determination unit 104 determines to use the highest (finest) resolution among the resolution of the first medical image, the resolution of the second medical image, and the first resolution as the resolution in the slice direction of the subtraction image. On the other hand, in a case where the resolution of the first medical image does not satisfy the first condition, the determination unit 104 determines to use the average value of the resolution of the first medical image, the resolution of the second medical image, and the first resolution as the resolution in the slice direction of the subtraction image.

(S2050) (Generate Subtraction Image)

In step S2050, the subtraction image generation unit 105 displaces each position on the second medical image to a position on the first medical image, based on the displacement field acquired in step S2030. Then, the difference image generation unit 105 generates a difference image by calculating a difference value of pixels between the displaced position and a corresponding position on the first medical image. In this processing, the difference image is generated at the output resolution determined in step S2030. Then, the difference image generation unit 105 outputs the generated difference image to the projection image generation unit 106 and the display control unit 107.

FIG. 3 illustrates an axial cross section 300 of the first medical image, an axial cross section 301 of the second medical image, and an axial cross section 302 of the subtraction image. The axial cross section 300 of the first medical image includes an abnormal region 303, and the axial cross section 302 of the subtraction image includes a subtraction area 304 corresponding to the abnormal region 303. The subtraction area 304 corresponding to the abnormal region 303 is an area drawn as a subtraction value of luminance between the first medical image and the second medical image since the second medical image does not include an abnormal region in an area corresponding to the abnormal region 303 existing in the first medical image. The resolution of the axial cross section 302 of the subtraction image matches the resolution of the axial cross section 300 of the first medical image, and thus these two images are associated with each other in voxel units. Consequently, for example, the images can be easily fused, and corresponding positions between images can be easily displayed in such a manner that if the subtraction area 304 is specified, the position of the abnormal region 303 corresponding to the original region is displayed.

(S2060) (Generate Subtraction Projection Image)

In step S2060, the projection image generation unit 106 generates the difference projection image that is obtained by two-dimensionally projecting a luminance of the difference image generated in step S2040. Then, the projection image generation unit 106 outputs the generated difference projection image to the display control unit 107.

More specifically, the projection image generation unit 106 generates a projection image obtained by projecting the subtraction image, which is a three-dimensional image, in parallel to the slice plane as the subtraction projection image. In a case where the original image of the subtraction image is an X-ray CT image, the slice direction coincides with a body axis direction (the Z-axis). Thus, the subtraction projection image is an image projected in a direction orthogonal to a body axis of a subject. For example, the projection image generation unit 106 generates the subtraction projection image projected to a front direction (the coronal direction) of the subject as the direction orthogonal to the body axis. Accordingly, information about the subtraction image of an entire imaging region of the subject can be easily recognized. As a projection method, for example, an image is generated by calculating an average value of a maximum value and a minimum value of luminance in a projection direction. In the following description, the image is referred to as a maximum intensity projection/minimum intensity projection image (MIP/MinIP image). Accordingly, a value considering both a positive subtraction value and a negative subtraction value in the subtraction image can be reflected on the projected image. The projection method is not limited to the above-described one and may be maximum intensity projection (MIP) or minimum intensity projection (MinIP). In other words, the subtraction projection image includes a MIP image, a MinIP image, or an image in which a value based on both a maximum value and a minimum value of a voxel value on a projection line is projected in a case where a three-dimensional image is two-dimensionally projected. In this processing, the resolution in the slice direction of the subtraction projection image is the output resolution determined in step S2030.

Figure 4:
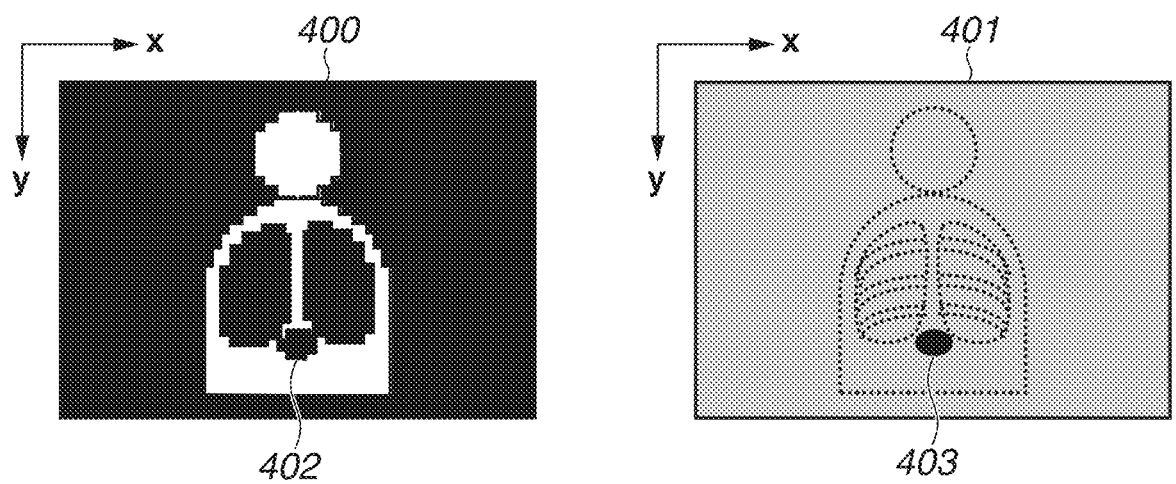
FIG. 4 is a diagram illustrating an example of a coronal cross section of an original image and a subtraction projection image.

FIG. 4 illustrates a coronal cross section image 400 and a subtraction projection image 401 of the first medical image. The coronal cross section image 400 of the first medical image includes an abnormal region 402, and a subtraction projection area 403 on the subtraction projection image 401 represents a projected subtraction area corresponding to the abnormal region 402. The subtraction projection area 403 corresponds to an area obtained by projecting a three-dimensional subtraction area including the subtraction area 304 in the slice image in FIG. 3 in the coronal direction. In FIG. 4, since the slice interval of the first medical image is large (for example, 5 mm), the resolution of the coronal cross section image 400 in the slice direction (the Z-axis in FIG. 4) becomes low. However, since the subtraction projection image 401 is an image which maintains the information amount of the subtraction in details regarding that the resolution in the slice direction is the processing resolution (for example, 1 mm), subtraction projection image 401 is not rough in the slice direction. In other words, the abnormal region 402 is rough in the coronal cross section image 400 since the slice interval of the first medical image is large, but the subtraction projection area 403 in the subtraction projection image 401 is finely drawn since the information amount of the subtraction in details is maintained.

(S2070) (Display Image)

In step S2070, the display control unit 107 performs control to display the cross sectional image of the subtraction image acquired from the subtraction image generation unit 105 and the subtraction projection image acquired from the projection image generation unit 106 on the display unit 150. The display control unit 107 also performs control to display the cross sectional images of the first medical image and the second medical image on the display unit 150.

The processing for displaying these images is not necessarily essential, and the generated subtraction image and subtraction projection image may be stored in a not-illustrated storage unit or may be output to the data server 130. Generation of the subtraction projection image is not necessarily essential, and the subtraction projection image may be generated by a different apparatus, based on the subtraction image stored in the image processing apparatus 100.

The processing of the image processing apparatus 100 is performed as described above.

According to the present exemplary embodiment, in a case where a projection image is generated by projecting a luminance value of a subtraction image in parallel to the slice plane, the projection image can be generated at a fine resolution in the slice direction even if a slice interval of an original image is large.

Accordingly, in a case where a projection image is generated by projecting using a luminance value of a subtraction image parallel to the slice plane as in NPL 1, the projection image can be generated with a fine resolution in the slice direction even if a slice interval of an original image is large.

Modification

According to the first exemplary embodiment, the upper limit value (the first resolution) in a case where the value in the slice direction of the output resolution and the processing resolution are matched with each other. However, the upper limit value of the output resolution and the processing resolution are not necessarily matched with each other. For example, the processing resolution may be a neighborhood value of the upper limit value of the output resolution. According to a modification, a neighborhood value is defined as a value within ±0.5 mm with respect to a target resolution. In other words, the neighborhood value is a value including the first resolution, based on the first resolution. For example, in step S2040, the upper limit value of the output resolution is set to the resolution (1 mm) at which the subtraction in details between the images can be calculated as described in step S2020. On the other hand, in step S2020, the processing resolution subjected to the resolution conversion is set to 1.5 mm, which is the neighborhood value of 1 mm. Then, in step S2030, registration is performed between the first conversion image of which the resolution is converted to 1.5 mm and the second conversion image. Accordingly, registration can be performed at high speed without deteriorating registration accuracy as much as possible (without reducing the information amount of the displacement field as much as possible) by performing registration at the resolution near 1 mm with respect to a case in which the resolution is converted to 1 mm. Then, in step S2050, the subtraction image having the upper limit value of 1 mm of the output resolution is generated using the displacement field having the resolution of 1.5 mm, and in step S2070, the subtraction projection image is generated based on the generated subtraction image. The information amount of the displacement field used for generating the subtraction image is not so reduced as compared with the case of the resolution of 1 mm. Thus, the subtraction projection image can be generated without much reducing the information amount in the slice direction. As described above, if the processing resolution is higher than the upper limit value of the output resolution but is the neighborhood value thereof, the subtraction projection image can be output at high speed without deteriorating a quality as much as possible with respect to the subtraction projection image generated according to the first exemplary embodiment.

Other Exemplary Embodiment

The technique described in the present specification can take an exemplary embodiment as, for example, a system, an apparatus, a method, a program, a recording medium (a storage medium), or the like. Specifically, the technique described in the present specification can be applied to a system including a plurality of devices (for example, a host computer, an interface device, an image capturing apparatus, and a web application) or an apparatus including a single device.

It is obvious that the technique described in the present specification can be achieved by the following configuration. More specifically, a recording medium (or a storage medium) storing a program code (a computer program) of software for realizing the functions of the above-described exemplary embodiments is supplied to a system or an apparatus. Needless to say, the storage medium is a computer-readable storage medium. A computer (or a central processing unit (CPU) or a micro processing unit (MPU)) of the system or the apparatus reads and executes the program code stored in the storage medium. In this case, the program code itself read out from the storage medium realizes the functions of the above-described exemplary embodiments, and the storage medium storing the program code constitutes the technique described in the present specification.

The present invention is not limited to the above-described exemplary embodiments and can be modified or changed in various ways without departing from the spirit and the scope of the present invention. Therefore, the following claims are attached in order to publicize the scope of the present invention.

According to the disclosure of the present specification, a subtraction image with high visibility can be generated even in a case where the subtraction image is projected in a direction parallel to a slice plane.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus that generates a three-dimensional image as a subtraction image from a first medical image and a second medical image which are three-dimensional images obtained by imaging a subject, the image processing apparatus comprising:
   an acquisition unit configured to acquire the first medical image and the second medical image;
   a determination unit configured to determine a resolution of the subtraction image; and
   a subtraction image generation unit configured to generate the subtraction image having the resolution determined by the determination unit,
   wherein the determination unit determines a resolution of at least one axial direction among three axial directions configuring the resolution of the subtraction image, based on a resolution of the first medical image and a predetermined first resolution.

2. The image processing apparatus according to claim 1, wherein the three-dimensional image is an image formed by a group of two-dimensional slice images, and
   wherein the determination unit determines a resolution in a slice direction orthogonal to a slice plane of the subtraction image, based on a resolution in the slice direction of the first medical image and the predetermined first resolution.

3. The image processing apparatus according to claim 2, wherein the determination unit determines the resolution in the slice direction of the subtraction image, based on a resolution that is a higher one of the resolution in the slice direction of the first medical image and the predetermined first resolution.

4. The image processing apparatus according to claim 2, wherein the determination unit determines the resolution in the slice direction of the subtraction image, based on a highest resolution among the resolution in the slice direction of the first medical image, a resolution in the slice direction of the second medical image, and the predetermined first resolution.

5. The image processing apparatus according to claim 2, wherein the determination unit determines the resolution in the slice direction of the subtraction image, based on an average value of the resolution in the slice direction of the first medical image and the predetermined first resolution.

6. The image processing apparatus according to claim 2, wherein the determination unit determines the resolution in the slice direction of the subtraction image, based on an average value of the resolution in the slice direction of the first medical image, the resolution in the slice direction of the second medical image, and the predetermined first resolution.

7. The image processing apparatus according to claim 2, wherein the determination unit determines a resolution in the slice plane of the subtraction image, based on a resolution in a slice plane of the first medical image.

8. The image processing apparatus according to claim 7, wherein the determination unit matches the resolution in the slice plane of the subtraction image with the resolution in the slice plane of the first medical image.

9. The image processing apparatus according to claim 1, further comprising:
   an alignment unit configured to convert respective resolutions of the first medical image and the second medical image to the predetermined first resolution or a neighborhood resolution of the predetermined first resolution and perform alignment processing between the first medical image and the second medical image, wherein the subtraction image generation unit generates the subtraction image, based on a result of the alignment processing.

10. The image processing apparatus according to claim 1, wherein, in a case where the resolution of the first medical image satisfies a first condition, the determination unit determines the resolution of the subtraction image, based on a highest resolution among the resolution of the first medical image, a resolution of the second medical image, and the predetermined first resolution, and in a case where the resolution of the first medical image does not satisfy the first condition, the determination unit determines a resolution in a direction of the subtraction image, based on an average value of the resolution of the first medical image, the resolution of the second medical image, and the predetermined first resolution.

11. The image processing apparatus according to claim 10, wherein the first condition is that the resolution of the first medical image is more than or equal to a first threshold value and is less than a second threshold value which is higher than the first threshold value.

12. The image processing apparatus according to claim 1, wherein the determination unit determines the resolution of at least one axial direction among the three axial directions configuring the resolution of the subtraction image as a resolution that is obtained by correcting the resolution of the first medical image based on the predetermined first resolution, and
wherein the subtraction image generation unit generates the subtraction image with reference to the first medical image using the resolution determined by the determination unit.

13. The image processing apparatus according to claim 1, further comprising:
an alignment unit configured to align a first conversion image and a second conversion image which are obtained by converting the resolution of the first medical image and a resolution of the second medical image to values based on the predetermined first resolution,
wherein the subtraction image generation unit generates the subtraction image, based on a result of the alignment.

14. The image processing apparatus according to claim 2, further comprising a projection image generation unit configured to generate a projection image by projecting the subtraction image in a direction parallel to the slice plane.

15. The image processing apparatus according to claim 14, wherein the projection image includes a maximum intensity projection (MIP) image, a minimum intensity projection (MinIP) image, or an image obtained by projecting using a value based on both of a maximum value and a minimum value of a pixel value on a projection line in a case where a three-dimensional image is two-dimensionally projected.

16. The image processing apparatus according to claim 1, wherein the first medical image and the second medical image are images captured at different times from each other.

17. The image processing apparatus according to claim 1, wherein the predetermined first resolution is a predetermined value equal to or more than 0.5 mm and equal to or less than 2.0 mm.

18. A method of image processing for generating a three-dimensional image as a subtraction image from a first medical image and a second medical image which are three-dimensional images obtained by imaging a subject, the method comprising:
acquiring the first medical image and the second medical image;
determining a resolution of the subtraction image; and
generating the subtraction image having the resolution determined by the determining,
wherein the determining determines a resolution of at least one axial direction among three axial directions configuring the resolution of the subtraction image, based on a resolution of the first medical image and a predetermined first resolution.

19. A non-transitory computer-readable storage medium storing a program that causes a computer to execute each unit in the image processing apparatus according to claim 1.

* * * * *